(12) United States Patent
Smith et al.

(10) Patent No.: US 9,752,968 B2
(45) Date of Patent: Sep. 5, 2017

(54) ROTATING SHIELDED MAGNETIC ACTUATOR

(71) Applicant: LUMINEX CORPORATION, Austin, TX (US)

(72) Inventors: Eric Smith, Austin, TX (US); Adam Schilffarth, Cedar Park, TX (US)

(73) Assignee: LUMINEX CORPORATION, Austin, TX (US)

( * ) Notice: Subject to any disclaimer, the term of this patent is extended or adjusted under 35 U.S.C. 154(b) by 453 days.

(21) Appl. No.: 14/132,823

(22) Filed: Dec. 18, 2013

(65) Prior Publication Data

US 2014/0179022 A1   Jun. 26, 2014

Related U.S. Application Data

(60) Provisional application No. 61/745,310, filed on Dec. 21, 2012.

(51) Int. Cl.
| | |
|---|---|
| *G01N 1/00* | (2006.01) |
| *G01N 1/40* | (2006.01) |
| *B01L 3/00* | (2006.01) |
| *B03C 1/033* | (2006.01) |
| *B03C 1/28* | (2006.01) |

(52) U.S. Cl.
CPC ......... *G01N 1/4044* (2013.01); *B01L 3/5085* (2013.01); *B03C 1/0332* (2013.01); *B03C 1/288* (2013.01); *B01L 2200/0668* (2013.01); *B01L 2300/0829* (2013.01); *B01L 2300/0851* (2013.01); *B03C 2201/18* (2013.01); *B03C 2201/26* (2013.01); *Y10T 436/25375* (2015.01)

(58) Field of Classification Search
CPC .................. G01N 1/4044; B01L 2400/043
USPC ...................................................... 436/177
See application file for complete search history.

(56) References Cited

U.S. PATENT DOCUMENTS

| | | | | |
|---|---|---|---|---|
| 5,108,574 | A * | 4/1992 | Kirs .................... | H01J 37/3441 204/192.12 |
| 2001/0030906 | A1* | 10/2001 | Friedman ............ | B01F 11/0008 366/114 |
| 2003/0040129 | A1 | 2/2003 | Shah ............................... | 506/32 |
| 2006/0057578 | A1 | 3/2006 | Willner et al. ............... | 435/6.11 |
| 2006/0082225 | A1 | 4/2006 | Korenaga et al. ......... | 310/12.06 |
| 2006/0201887 | A1* | 9/2006 | Siddiqi ............... | B01F 13/0809 210/695 |
| 2008/0290741 | A1 | 11/2008 | Cardon et al. ............. | 310/12.06 |

(Continued)

FOREIGN PATENT DOCUMENTS

WO   WO 2009/013683   1/2009

OTHER PUBLICATIONS

International Search Report and Written Opinion, issued in PCT/US2013/076141, dated Apr. 9, 2014.
(Continued)

*Primary Examiner* — Christine T Mui
*Assistant Examiner* — Emily Berkeley
(74) *Attorney, Agent, or Firm* — Parker Highlander PLLC

(57) ABSTRACT

Systems configured to isolate particles in a fluid assay are disclosed. Methods for collecting a sample of magnetic particles from a liquid are also disclosed. In certain embodiments, the disclosed systems and methods include a magnetic actuator coupled to a chassis, where the magnetic actuator comprises at least one shielded rotatable magnet.

8 Claims, 10 Drawing Sheets

(56) References Cited

U.S. PATENT DOCUMENTS

| | | | |
|---|---|---|---|
| 2009/0191638 A1* | 7/2009 | Schilffarth | B01L 3/502761 |
| | | | 436/50 |
| 2010/0068764 A1 | 3/2010 | Sista et al. | 435/79 |
| 2010/0075430 A1 | 3/2010 | Hofstadler et al. | 436/94 |
| 2011/0012440 A1 | 1/2011 | Toyota et al. | 310/12.24 |
| 2012/0184037 A1 | 7/2012 | Schilffarth et al. | 436/50 |

OTHER PUBLICATIONS

International Search Report and Written Opinion, issued in PCT/US2013/076464, dated Apr. 7, 2014.

* cited by examiner

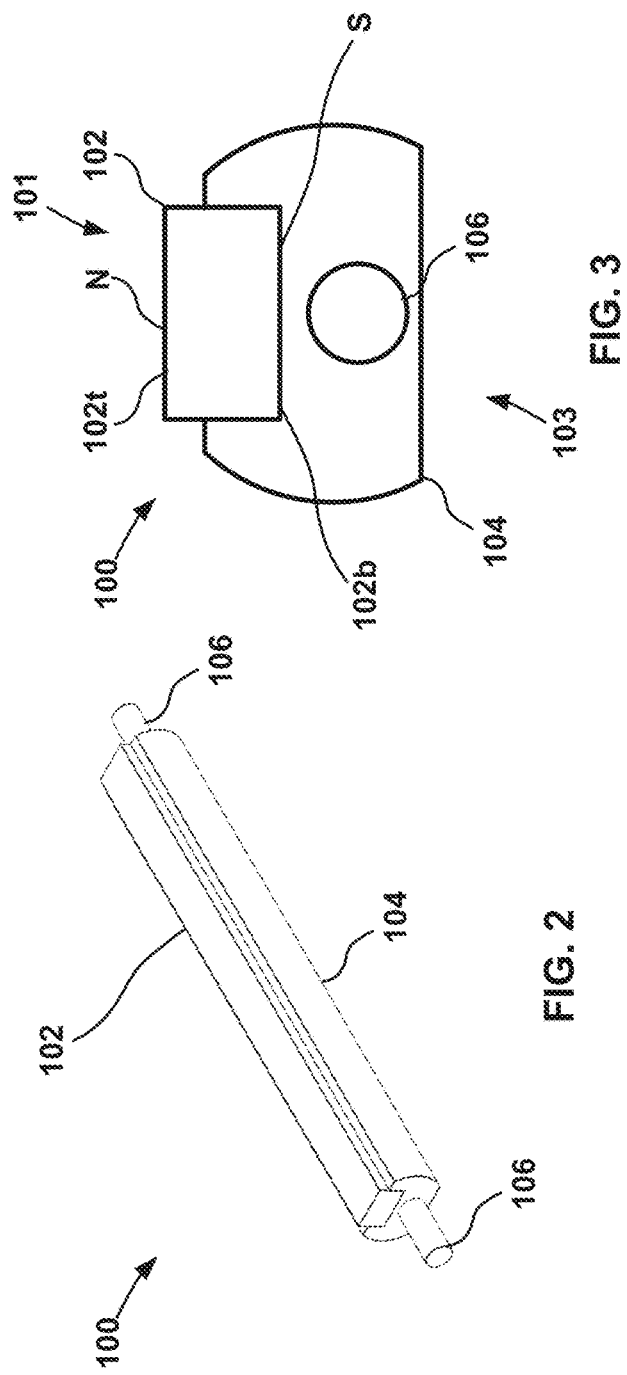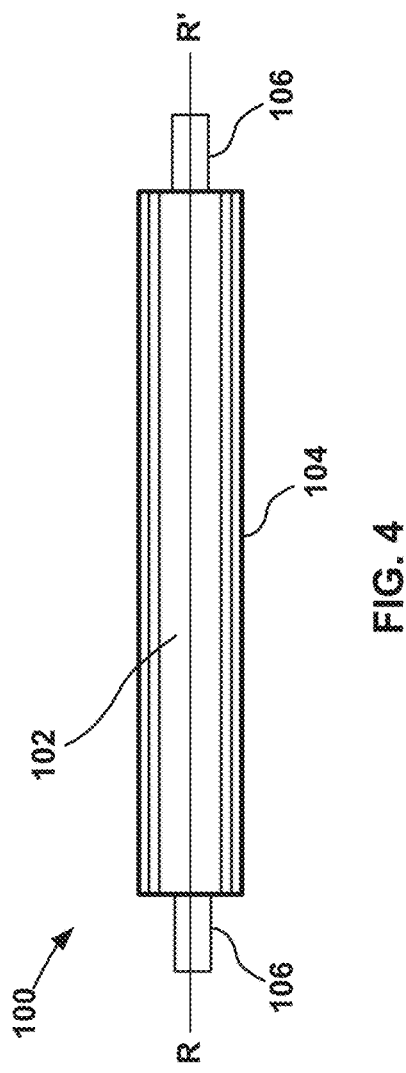

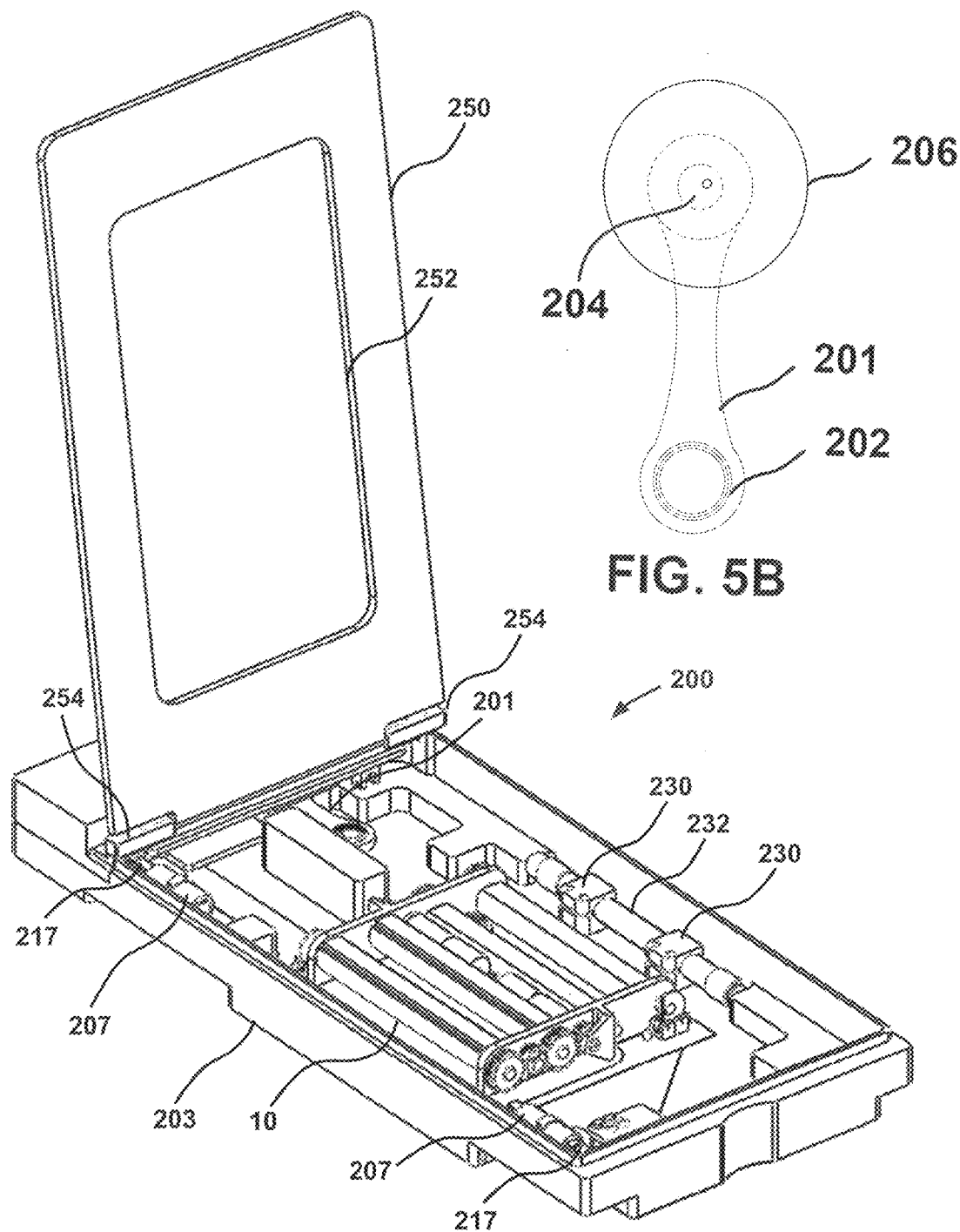

```
1000 ──┐  ┌──────────────────────────────────────────────────────────┐
        │  │ OBTAINING A SYSTEM COMPRISING:                           │
        │  │    A CHASSIS;                                            │
        │  │    A MAGNETIC ACTUATOR COUPLED TO THE CHASSIS;           │
        │  │    A TUB COUPLED TO THE CHASSIS;                         │
        │  │    AN AGITATOR MOTOR COUPLED TO THE CHASSIS AND          │
        │  │        CONFIGURED TO AGITATE THE TUB; AND                │
  1002 ─┤  │    A WELL PLATE COUPLED TO THE TUB AND COMPRISING A      │
           │        PLURALITY OF WELLS ARRANGED IN COLUMNS AND        │
           │        ROWS;                                             │
           │    WHERE THE TUB IS CONFIGURED TO SUPPORT THE WELL       │
           │        PLATE SUCH THAT EACH SHIELDED MAGNET IS ADJACENT  │
  1004 ─┐  │        TO AT LEAST ONE COLUMN OF WELLS.                  │
         └──┴──────────────────────────────────────────────────────────┘
           ┌──────────────────────────────────────────────────────────┐
  1006 ────│ OBTAINING A FIRST SUSPENSION COMPRISING A PLURALITY OF   │
           │ MAGNETIC BEADS IN SUSPENSION IN A FIRST LIQUID           │
           ├──────────────────────────────────────────────────────────┤
           │ INTRODUCING A VOLUME OF THE FIRST SUSPENSION INTO AT LEAST│
           │ ONE WELL                                                 │
  1008 ────├──────────────────────────────────────────────────────────┤
           │ ROTATING THE SHIELDED MAGNETS TO A MAX POSITION SUCH THAT│
           │ EACH PERMANENT MAGNET EXERTS A MAGNETIC FORCE ON AT      │
  1010 ────│ LEAST ONE COLUMN OF WELLS                                │
           ├──────────────────────────────────────────────────────────┤
  1012 ────│ FORMING A PELLET OF MAGNETIC BEADS IN AT LEAST ONE WELL  │
           ├──────────────────────────────────────────────────────────┤
           │ ASPIRATING A PORTION OF THE FIRST LIQUID FROM AT LEAST ONE│
           │ WELL                                                     │
  1014 ────├──────────────────────────────────────────────────────────┤
           │ ROTATING THE SHIELDED MAGNETS TO A MIN POSITION SUCH THAT│
           │ SUBSTANTIALLY NO MAGNETIC FORCE IS EXERTED ON ANY COLUMN │
  1016 ────│ OF WELLS                                                 │
           ├──────────────────────────────────────────────────────────┤
  1018 ────│ OBTAINING A SECOND LIQUID                                │
           ├──────────────────────────────────────────────────────────┤
           │ INTRODUCING THE SECOND LIQUID INTO AT LEAST ONE WELL     │
           │ COMPRISING MAGNETIC BEADS                                │
  1020 ────├──────────────────────────────────────────────────────────┤
           │ AGITATING THE MAGNETIC BEADS IN AT LEAST ONE WELL TO FORM│
           │ A SECOND SUSPENSION COMPRISING THE MAGNETIC BEADS        │
           │ SUSPENDED IN THE SECOND LIQUID                           │
           └──────────────────────────────────────────────────────────┘
```

FIG. 12

ROTATING SHIELDED MAGNETIC ACTUATOR

CROSS REFERENCE TO RELATED APPLICATIONS

This application claims priority to U.S. Provisional Patent Application Ser. No. 61/745,310, filed Dec. 21, 2012, the contents of which are incorporated by reference herein.

TECHNICAL FIELD

Embodiments of the present disclosure relate to rotating shielded magnetic actuators. Particular embodiments relate to rotating shielded magnetic actuators configured to isolate magnetic particles in a fluid assay. Embodiments of the rotating magnet arrays disclosed herein are configured for use with a well plate comprising a plurality of wells in order to isolate a magnetic particles in a fluid assay.

BACKGROUND

The following descriptions and examples are not admitted to be prior art by virtue of their inclusion within this section.

Fluid assays are used for a variety of purposes, including but not limited to biological screenings and environmental assessments. Often, particles (sometimes known as "beads" or "microspheres") are used in fluid assays to aid in the detection of analytes of interest within a sample. In particular, these particles provide a substrate for carrying reagents configured to react with analytes of interest within a sample such that the analytes may be detected. In many cases, magnetic materials are incorporated into particles such that the particles may be immobilized by magnetic fields during the preparation and/or analysis of a fluid assay. In particular, particles may be immobilized during an assay preparation process such that excess reagents and/or reactionary byproducts superfluous to the impending assay may be removed. In addition or alternatively, particles may be immobilized during analysis of a fluid assay such that data relating to analytes of interest in the assay may be collected from a fixed object.

Immobilization is typically performed for only a fraction of the time used to prepare or analyze an assay such that the particles may be allowed to be suspended in or allowed to flow with the assay. In addition, the immobilization may be performed once or multiple times during the preparation or analysis of a fluid assay depending on the specifications of the process. For such reasons, it is generally necessary to intermittently introduce and retract a magnetic actuator in the vicinity of a vessel comprising the magnetic particles. In some cases, however, the inclusion of a magnetic actuation device within a fluid assay system may complicate the design of the system, particularly hindering the ability to introduce assay/sample/reagent plates and/or vessels into the system.

SUMMARY OF THE INVENTION

Disclosed are embodiments of magnetic actuators, systems comprising such magnetic actuators, and methods of using such actuators and systems. In one embodiment, a magnetic actuator configured to isolate particles in a fluid assay is disclosed, the magnetic actuator comprising: a first shielded magnet comprising a first shield coupled to and covering a portion of a first permanent magnet, where the first shielded magnet has a thickness, a length, and a first axis of rotation; a motor coupled to the first shielded magnet and configured to rotate the first shielded magnet about the axis of rotation; and a lateral support member configured to support the first shielded magnet and the motor. In certain embodiments, the axis of rotation is an eccentric axis of rotation.

In some embodiments, the magnetic actuator further comprises a second shielded magnet comprising a second shield coupled to and covering a portion of a second permanent magnet, where the second shielded magnet has a thickness, a length, and a second axis of rotation. In still other embodiments, the second shielded magnet is coupled to the first shielded magnet such that rotation of the first shielded magnet about the first axis of rotation rotates the second shielded magnet about the second axis of rotation. In some embodiments, the first permanent magnet may be magnetized through its thickness. In specific embodiments, the first permanent magnet may comprise a rare earth material, including for example, neodymium. In other specific embodiments, the first shield may comprise a magnetic permeable material, including for example, 1018 cold rolled steel.

In other embodiments, a magnetic actuator configured to isolate particles in a fluid assay is disclosed, the magnetic actuator comprising: a first pair of shielded magnets rotatable together, each shielded magnet comprising a shield coupled to and covering at least a portion of a permanent magnet, where each shielded magnet has a thickness, a length, and an axis of rotation; a first motor coupled to the first pair of shielded magnets through a gearset and configured to rotate the first pair of shielded magnets about their respective axes of rotation; a second pair of shielded magnets rotatable together, each shielded magnet comprising a shield coupled to and covering a portion of a permanent magnet, where each shielded magnet has a thickness, a length, and an axis of rotation; and a second motor coupled to the second pair of shielded magnets through a gearset and configured to rotate the second pair of shielded magnets about their respective axes of rotation. In certain embodiments, each axes of rotation is an eccentric axis of rotation.

In still other embodiments, a system is disclosed, the system being configured to isolate particles in a fluid assay and comprising: a chassis; a magnetic actuator coupled to the chassis, the magnetic actuator having rotatable shielded magnets; a tub coupled to the chassis; and a well plate coupled to the tub and comprising a plurality of wells arranged in columns and rows; where the tub is configured to support the well plate such that each shielded magnet is adjacent to at least one column of wells.

In certain embodiments, a rotatable shielded magnet is configured to rotate from a first position to a second position; the rotatable shielded magnet exerts a first magnetic field on the well plate in the first position; the rotatable shielded magnet exerts a second magnetic field on the well plate in the second position; and the first magnetic field is greater than the second magnetic field. In particular embodiments, at least one well comprises a plurality of magnetic microspheres; the first magnetic field is sufficient to move the plurality of magnetic microspheres; and the second magnetic field is not sufficient to move the plurality of magnetic microspheres.

In some embodiments, each rotatable shielded magnet is adjacent to two columns of wells. In other embodiments, each rotatable shielded magnet comprises a shield coupled to and covering a portion of a permanent magnet, where each rotatable shielded magnet has a thickness, a length, and an axis of rotation, which may be an eccentric axis of rotation. In certain embodiments, the shields comprise a magnetic permeable material, the permanent magnets comprise a rare earth material, and the permanent magnets are magnetized through their thickness.

In some embodiments, the system further comprises an agitator motor and a link coupled to the tub, where the agitator and the link are configured to agitate the tub and the well plate during operation.

In other embodiments, a method for collecting a sample of magnetic particles from a liquid is disclosed, comprising: a chassis; a magnetic actuator coupled to the chassis, the magnetic actuator having rotatable shielded magnets a tub coupled to the chassis; and a well plate coupled to the tub and comprising a plurality of wells arranged in columns and rows; where the tub is configured to support the well plate such that each shielded magnet is adjacent to at least one column of wells; obtaining a first suspension comprising a plurality of magnetic particles suspended in a first liquid; introducing a volume of the first suspension into at least one well; adjusting the shielded magnets to a first position such that a magnetic force is exerted on at least one column of wells; forming a pellet of magnetic particles in at least one well; and aspirating a portion of the first liquid from at least one well.

In some embodiments, the method further comprises rotating the shielded magnets to a second position such that substantially no magnetic force is exerted on any column of wells. In other embodiments, the method further comprises obtaining a second liquid and introducing the second liquid into at least one well comprising magnetic particles.

In still other embodiments, the method further comprises agitating the magnetic particles in at least one well to form a second suspension comprising the magnetic particles suspended in the second liquid.

Non-limiting examples of magnetic particles that may be used in connection with the methods and systems described herein include magnetic nanoparticles and magnetic microspheres (sometimes referred to as "beads"). As used herein, the term "nanoparticles" refers to particles with a diameter of less than 1 micrometer. In certain embodiments the nanoparticles have a diameter between 5-500 nanometers. Magnetic microspheres typically have a diameter in the range of 1-500 micrometers. In certain embodiments, the magnetic microspheres have a diameter in the range of 5-25 micrometers. The magnetic particles may be coated with or coupled to functional groups to enhance the isolation of particular components from a sample. For example magnetic silica particles or magnetic glass particles may be employed for the isolation of nucleic acids from a sample. Magnetic particles coupled to, for example, oligonucleotides or antibodies may be used to isolate a particular target nucleic acid or protein, respectively.

The term "coupled" is defined as connected, although not necessarily directly, and not necessarily mechanically.

The terms "a" and "an" are defined as one or more unless this disclosure explicitly requires otherwise.

The term "substantially" and its variations (e.g. "approximately" and "about") are defined as being largely but not necessarily wholly what is specified (and include wholly what is specified) as understood by one of ordinary skill in the art. In any disclosed embodiment, the terms "substantially," "approximately," and "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features. For example, a magnetic actuator that comprises a shielded magnet possesses at least one shielded magnet, but may possess more than one shielded magnet.

Furthermore, a device or structure that is configured in a certain way is configured in at least that way, but may also be configured in ways that are not listed. Metric units may be derived from the English units provided by applying a conversion factor.

The feature or features of one embodiment may be applied to other embodiments, even though not described or illustrated, unless expressly prohibited by this disclosure or the nature of the embodiments.

Any embodiment of any of the disclosed devices and methods can consist of or consist essentially of—rather than comprise/include/contain/have—any of the described elements and/or features and/or steps. Thus, in any of the claims, the term "consisting of" or "consisting essentially of" can be substituted for any of the open-ended linking verbs recited above, in order to change the scope of a given claim from what it would otherwise be using the open-ended linking verb.

Other features and associated advantages will become apparent with reference to the following detailed description of specific embodiments in connection with the accompanying drawings.

BRIEF DESCRIPTION OF THE DRAWINGS

The following drawings illustrate by way of example and not limitation. For the sake of brevity and clarity, every feature of a given structure may not be labeled in every figure in which that structure appears. Identical reference numbers do not necessarily indicate an identical structure. Rather, the same reference number may be used to indicate a similar feature or a feature with similar functionality, as may non-identical reference numbers. The embodiments of the present rotating magnetic actuators and their components shown in at least FIGS. 1, 5A, and 6-9 are drawn to scale.

FIG. 1 is an isometric view of an embodiment of a magnetic actuator.

FIG. 2 is an isometric view of an embodiment of a shielded magnet of the embodiment of FIG. 1.

FIG. 3 is an end view of the embodiment of FIG. 2.

FIG. 4 is a top view of the embodiment of FIG. 2.

FIG. 5A is a perspective view of an embodiment of an assay preparation module showing the chassis and the embodiment of FIG. 1.

FIG. 5B is a top view of an embodiment of an agitator motor coupled to a link of the embodiment of FIG. 5A.

FIG. 6 is a perspective view of the embodiment of FIG. 5A showing the chassis and the tub coupled to the chassis.

FIG. 7 is a perspective view of the embodiment of FIG. 5A showing the chassis and an embodiment of a wellplate coupled to the chassis.

FIG. 8 is a perspective view of the embodiment of FIG. 5A showing the lid in the closed position.

FIG. 9 is an end view of a portion of the embodiment of FIG. 5A and a well plate showing shielded magnets in a first position.

FIG. 12 is an embodiment of a method for collecting a sample of magnetic particles from a liquid.

DETAILED DESCRIPTION

Figure 1:
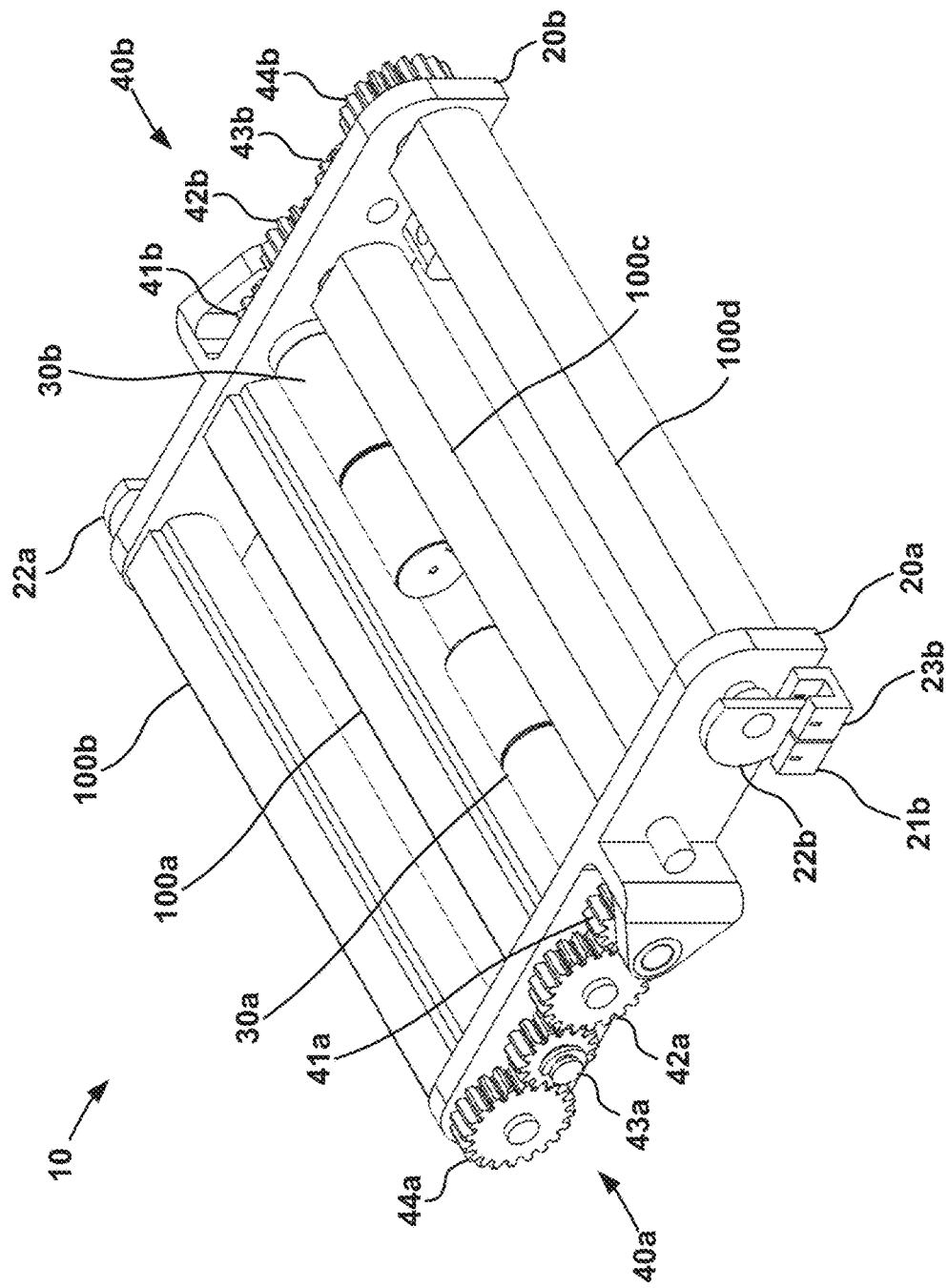

Various features and advantageous details are explained more fully with reference to the non-limiting embodiments that are illustrated in the accompanying drawings and detailed in the following description. It should be understood, however, that the detailed description and the specific examples, while indicating embodiments of the invention, are given by way of illustration only, and not by way of limitation. Various substitutions, modifications, additions, and/or rearrangements within the spirit and/or scope of the underlying inventive concept will become apparent to those of ordinary skill in the art from this disclosure.

In the following description, numerous specific details are provided to provide a thorough understanding of the disclosed embodiments. One of ordinary skill in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The following figures illustrate embodiments of magnetic actuators, fluid assay systems comprising such magnetic actuators, and methods employing such magnetic actuators. In the following illustrations, numbers are used to indicate a generic structure or feature while letters are used to indicate specific instances of that structure or feature. For example, a generic shielded magnet is referred to with reference numeral 100, while a first shielded magnet is referred to with reference numeral 100a. Descriptions of the generic shielded magnet 100 also pertain to the specific instance of the shielded magnet, e.g. first shielded magnet 100a.

Magnetic Actuator

FIG. 1 shows an isometric view of magnetic actuator 10, one embodiment of the present magnetic actuators. Actuator 10 comprises at least one shielded magnet coupled to a rotation motor, e.g. a motor configured to rotate at least one shielded magnet. In the illustrated embodiment, actuator 10 comprises four shielded magnets 100a, 100b, 100c, and 100d. In this embodiment, pairs of shielded magnets are coupled to a rotation motor via a gearset such that one rotation motor moves two shielded magnets. For example, in the illustrated embodiment, first rotation motor 30a is coupled to first shielded magnet 100a and second shielded magnet 100b via first gearset 40a. Second rotation motor 30b is coupled to third shielded magnet 100c and fourth shielded magnet 100d via second gearset 40b. Paired shielded magnets of actuator 10 move in substantially the same direction at substantially the same time when actuated by a rotation motor (e.g., the paired magnets move synchronously). Thus, first shielded magnet 100a and second shielded magnet 100b, which are paired, move in substantially the same direction at substantially the same time when actuated by first rotation motor 30a. Third shielded magnet 100c and fourth shielded magnet 100d, which are also paired, move in substantially the same direction at substantially the same time when actuated by second rotation motor 30b.

The shielded magnets and motors of actuator 10 are supported by lateral support members 20a and 20b. In the illustrated embodiment, rotation motors 30a and 30b are positioned between lateral support members 20a and 20b and adjacent to at least one shielded magnet. In other embodiments, rotation motors 30 may be positioned outside the lateral support members and need not be adjacent to a shielded magnet.

First gearset 40a depicted in FIG. 1 comprises a first gear 41a coupled to rotation motor 30a. First gear 41a is coupled to second gear 42a, which is coupledto first shielded magnet 100a such that rotation of second gear 42a rotates first shielded magnet 100a. Second gear 42a is coupled to third gear 43a, which is rotatably coupled to lateral support member 20a. Third gear 43a is coupled to fourth gear 44a, which is coupled to second shielded magnet 100b such that rotation of fourth gear 44a rotates second shielded magnet 100b.

Second gearset 40b operates similarly to rotate third shielded magnet 100c and fourth shielded magnet 100d. First gear 41b is coupled to second gear 42b, which is coupled to third shielded magnet 100c such that rotation of second gear 42b rotates third shielded magnet 100c. Second gear 42b is coupled to third gear 43b, which is rotatably coupled to lateral support member 20b. Third gear 43b is coupled to fourth gear 44b, which is coupled to fourth shielded magnet 100d such that rotation of fourth gear 44b rotates fourth shielded magnet 100d.

FIGS. 2-4 show isometric, end, and top views respectively of an embodiment of shielded magnet 100. The depicted embodiment of shielded magnet 100 has a top side 101 and a bottom side 103. In the illustrated embodiment, shielded magnet 100 comprises a permanent magnet 102 coupled to a shield 104. Permanent magnet 102 is a substantially rectangular prism in the embodiment shown and comprises a top surface 102t and a bottom surface 102b. In other embodiments, permanent magnet 102 may be substantially cylindrical, semi-cylindrical, or another partially-cylindrical shape, such as any solid formed by the intersection of a cylinder and at least one plane parallel to the major axis of the cylinder.

Though not shown, in certain specific embodiments, permanent magnet 102 may be substantially rectangularly prismatic except that top surface 102t is convexly curved. In some of these embodiments, the curvature of top surface 102t is concentric with the rotational axis of the shielded magnet 102.

Shield 104 is coupled to permanent magnet 102 such that shield 104 covers at least a portion of permanent magnet 102. As used here, a "shield" substantially eliminates or substantially reduces transmission of the magnetic field of the permanent magnet to which it is coupled.

In the embodiment shown, shield 104 covers bottom surface 102b of permanent magnet 102. Axles 106 are coupled to shield 104 and are configured to be received by lateral support members 20a and 20b and coupled to gears such as first gear 41a or 41b, second gear 42a or 42b, third gear 43a or 43b, or fourth gear 44a or 44b; or coupled to a position indicator, such as position indicator 22a and 22b (shown in FIG. 1); or both. In the embodiment shown, axles 106 are located nearer bottom side 103 than top side 101 such that shielded magnet 100 has an eccentric axis of rotation R-R'.

In the illustrated embodiment, permanent magnet 102 comprises a rare earth material. In a specific embodiment, permanent magnet 102 may comprise grade N52 neodymium, though other materials having a high magnetic flux density may be used. Permanent magnet 102 is magnetized through its thickness as shown in FIG. 3. In the embodiment shown, the N pole is at the top surface 102*t* and the S pole is at bottom surface 102*b*. These polarities may be reversed in other embodiments.

Shield 104 comprises a magnetic permeable material in the illustrated embodiment. In certain embodiments, shield 104 may comprise 1018 cold rolled steel, while other suitable materials having high magnetic permeability and high magnetic saturation, such as mu-metal, may be used in addition or alternatively in other embodiments.

Assay Preparation Module

FIGS. 5A-8 are isometric views of assay preparation module 200, which is one embodiment of the present systems configured to isolate particles in a fluid assay. Module 200 comprises magnetic actuator 10.

Figure 6:
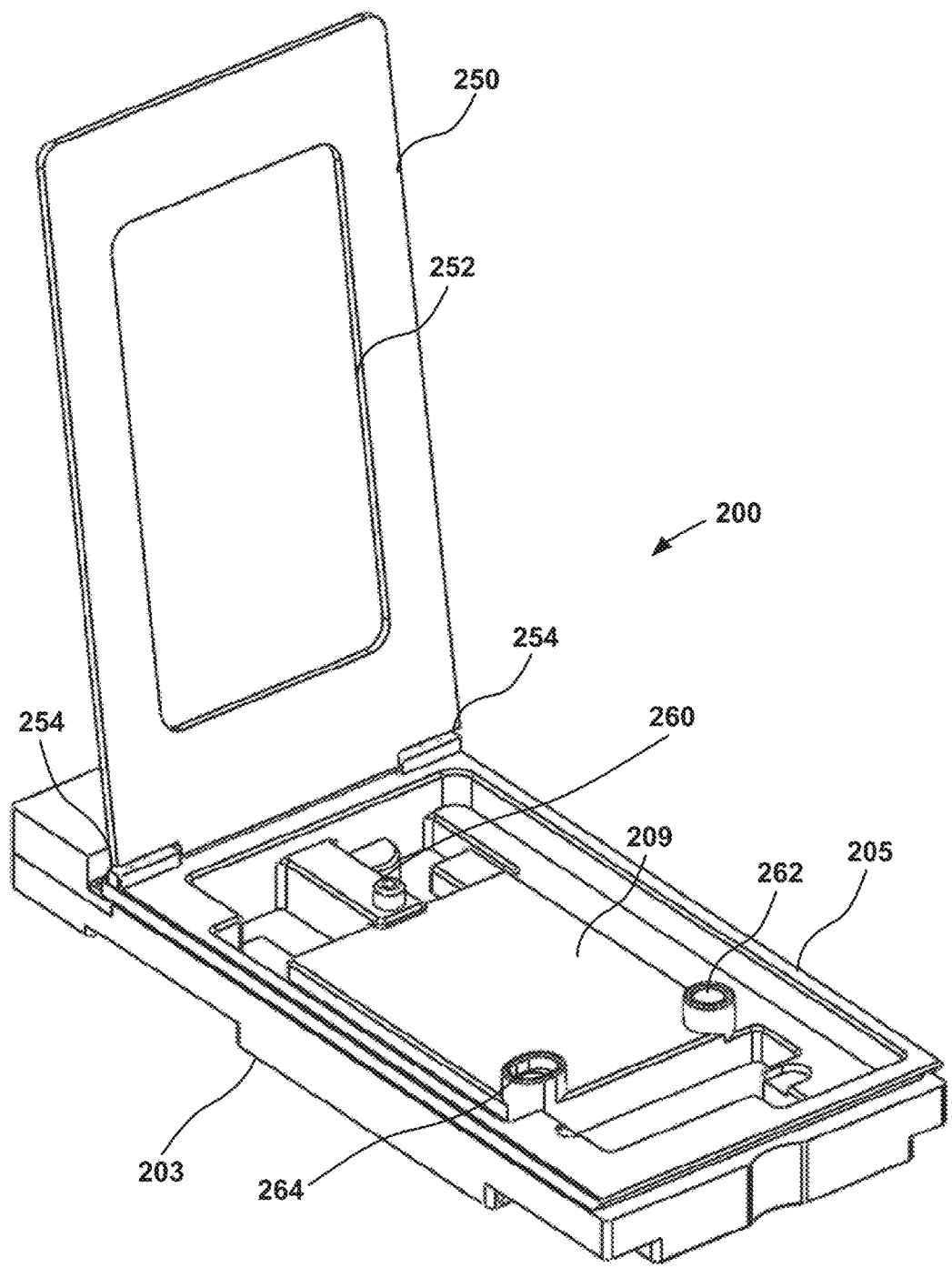

As shown in FIG. 5A, assay preparation module 200 comprises chassis 203, which is configured to be coupled to a tub 205 (shown in FIG. 6). In the illustrated embodiment, module 200 also includes lid 250, which is coupled to chassis 203 with hinges 254 that allow lid 250 to open and close. Lid 250 may be held closed with known latching mechanisms (e.g., a magnetic or electromagnetic latch, a clip, a tab and slot, etc.). Lid 250 is configured to retain at least a portion of tub 205 and/or well plate 210—also parts of module 200—while allowing access to reaction wells 220 of well plate 210. In the illustrated embodiment, lid 250 comprises window 252. In the preferred embodiment, window 252 is open and configured to allow access to a plurality of reaction wells 220 when lid 250 is in the down position (e.g., to allow fluids to be dispensed to one or more wells 220). In other embodiments, window 252 may be covered in a light-permeable material, where "light" includes the visible spectrum as well as ultraviolet light and infrared light.

Chassis 203 is configured to support embodiments of actuator 10 as discussed above. In some embodiments, actuator 10 may be coupled to chassis 203 via screws, adhesive, tabs and slots, ultrasonic welding, or other known joining methods. In other embodiments, portions of actuator 10 such as lateral support members 20*a* and 20*b*, may be integral to or form a portion of chassis 203. In addition, as shown the illustrated embodiment, chassis 203 also comprises an agitator motor 206 coupled to a link 201 (shown in FIG. 5B), two floating rails 217, and fixed rail 232. Each floating rail 217 is coupled to chassis 203 and to a bushing 207, while fixed rail 232 is coupled to chassis 203 via rail supports 230 in the embodiment shown.

In the illustrated embodiment of assay preparation module 200, agitator motor 206 is configured to agitate (e.g., shake, vibrate, oscillate, etc.) tub 205 via link 201 after receiving an electric signal. In an exemplary embodiment, link 201 contains an eccentric cam 204 fixed to the shaft of agitator motor 206 that is configured to convert rotation motion of agitator motor 206 into linear displacement of link 201 relative to agitator motor 206. In certain embodiments, link 201 can be configured for a maximum relative displacement of between about 0.25 mm and about 5.0 mm. Agitator motor 206 can be configured for a rotational speed of between about 10 RPM and about 1800 RPM in particular embodiments.

FIG. 6 shows an embodiment of assay preparation module 200 with tub 205 coupled to chassis 203. In the embodiment shown, link 201 is configured to receive a portion of tub 205 and transfer reciprocating force to tub 205; in particular, link 201 includes opening 202 that is configured to receive a portion of tub 205, such as a post or tab or other protrusion from the underside of tub 205. In various embodiments, tub 205 comprises holes, slots, channels, or other features that are configured to receive at least a portion of floating rails 217 and bushings 207, as well as a portion of fixed rail 232. In certain embodiments, bushings 207 may be coupled to tub 205 such as with a force fit.

In the embodiment shown, fixed rail 232 is configured to vertically support tub 205 and allow tub 205 to move in substantially one direction, such as back and forth along the length of fixed rail 232. Clearance exists between tub 205 and chassis 203 such that tub 205 may move relative to chassis 203. In this embodiment, floating rails 217 and bushings 207 are slidably retained within tub 205 and are configured to vertically support tub 205 and allow tub 205 to move in substantially two directions—longitudinally along length of rails 217 and laterally perpendicularly to the longitudinal and vertical directions. In the illustrated embodiment, each bushing 207 is configured to be coupled to tub 205 and further configured to move longitudinally relative to each floating rail 217.

Tub 205 is configured to be coupled to well plate 210, in particular embodiments, tub 205 comprises a circular slot 262 and an elliptical slot 264. Each slot is configured to receive a portion of well plate 210 such as posts or tabs or other protrusions from the underside of well plate 210.

The illustrated embodiment of tub 205 also comprises orientation post 260, which is configured to receive a portion of well plate 210 and/or be received by well plate 210. Orientation post 260 and/or slots 262 and 264 may comprise a sensor (e.g., a capacitive sensor, not shown) configured to detect the position of tub 205. For example, the sensor may be configured to detect that tub 205 is tilted, skewed, or otherwise misaligned, and send a signal to a processor indicating the position of tub 205 relative to the instrument containing the assay preparation module. Additionally, the sensor or sensors coupled to orientation post 260 and/or slots 262 and 264 may be configured to detect the presence of well plate 210.

In the embodiment shown, tub 205 comprises a well plate platform 209 upon which a well plate 210 (shown in FIG. 7) may be placed for additional vertical support. When well plate 210 is placed on, coupled to, or otherwise located on well plate platform 209, well plate 210 is considered to be adjacent to magnetic actuator 10.

In certain embodiments, tub 205 or portions of tub 205 (e.g., well plate platform 209) may comprise aluminum or another material configured to allow capacitive sensing.

Figure 7:
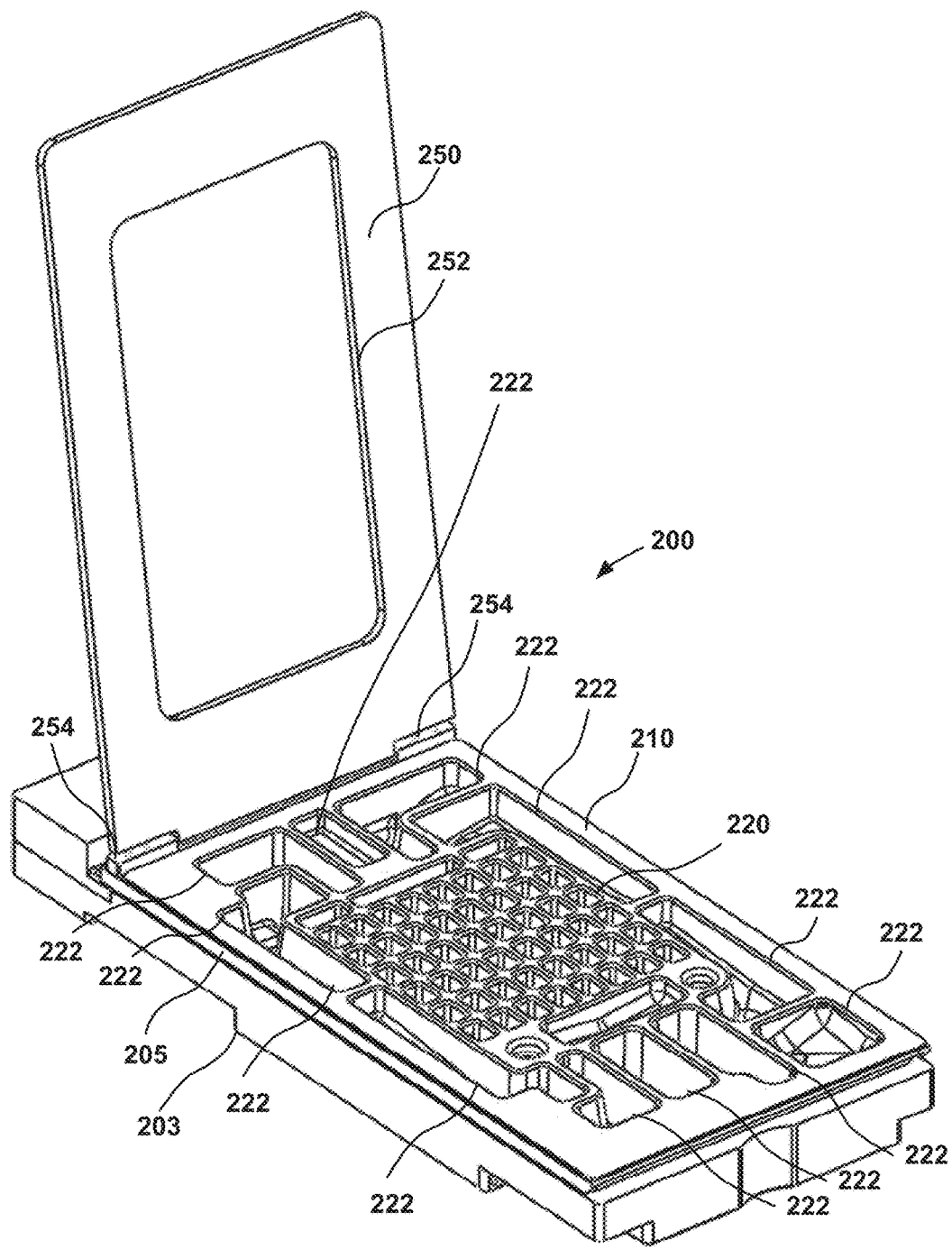
Figure 8:
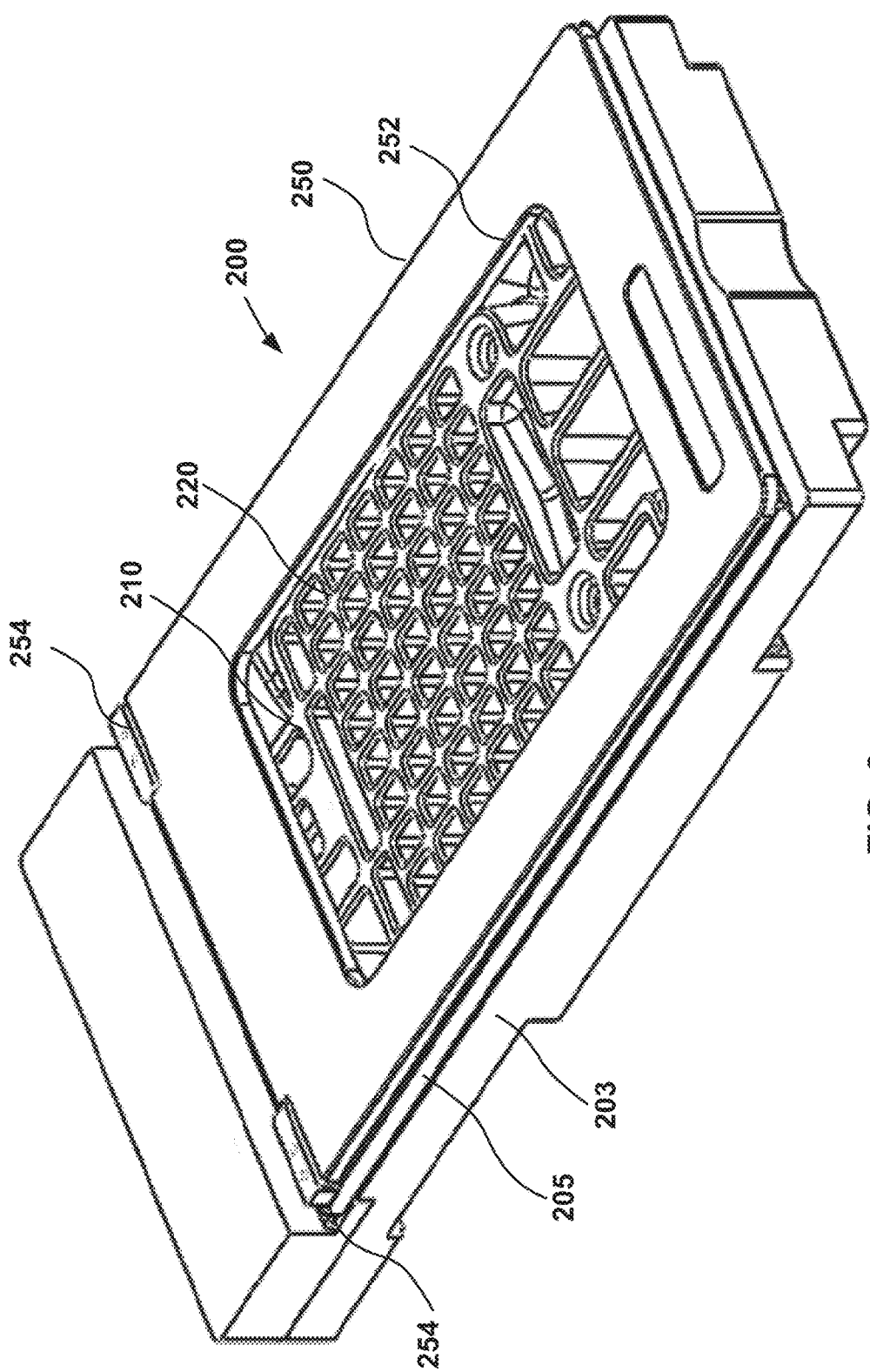
Figure 11:
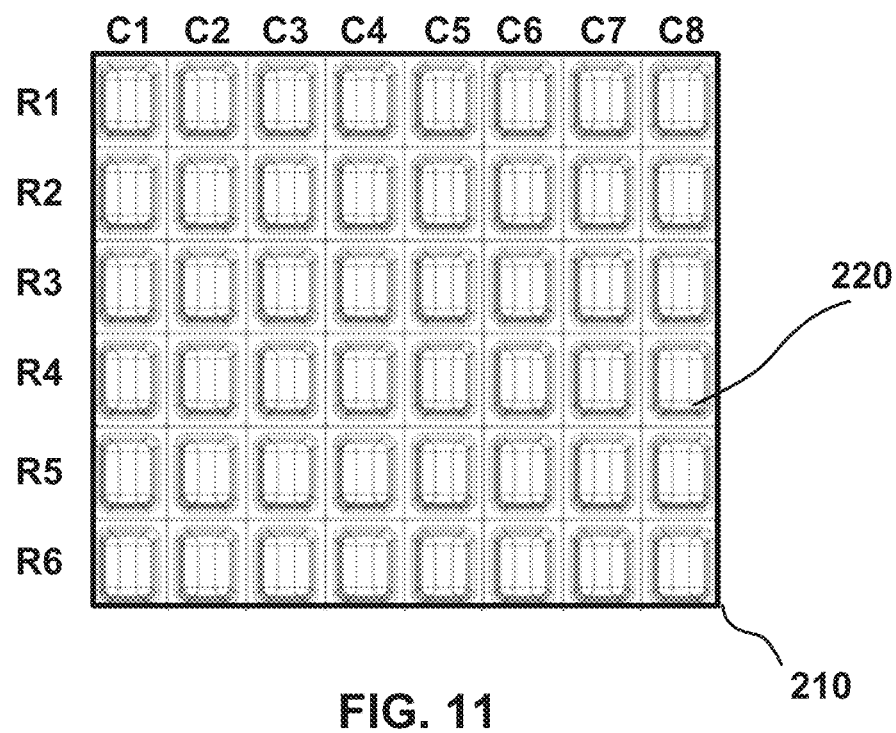
FIG. 11 is an embodiment of a portion of a well plate comprising a plurality of wells arranged in columns and rows.

FIG. 7 shows an embodiment of assay preparation module 200 with well plate 210 coupled to tub 205 and chassis 203. The illustrated embodiment of well plate 210 comprises a plurality of reaction wells 220 as well as a plurality of reservoirs 222. A more detailed view of an embodiment of reaction wells 220 is depicted in FIG. 11. FIG. 8 shows an embodiment of assay preparation module 200 with lid 250 in the down position with reaction wells 220 visible through window 252.

Assay Preparation Module and Well Plates

Figure 9:
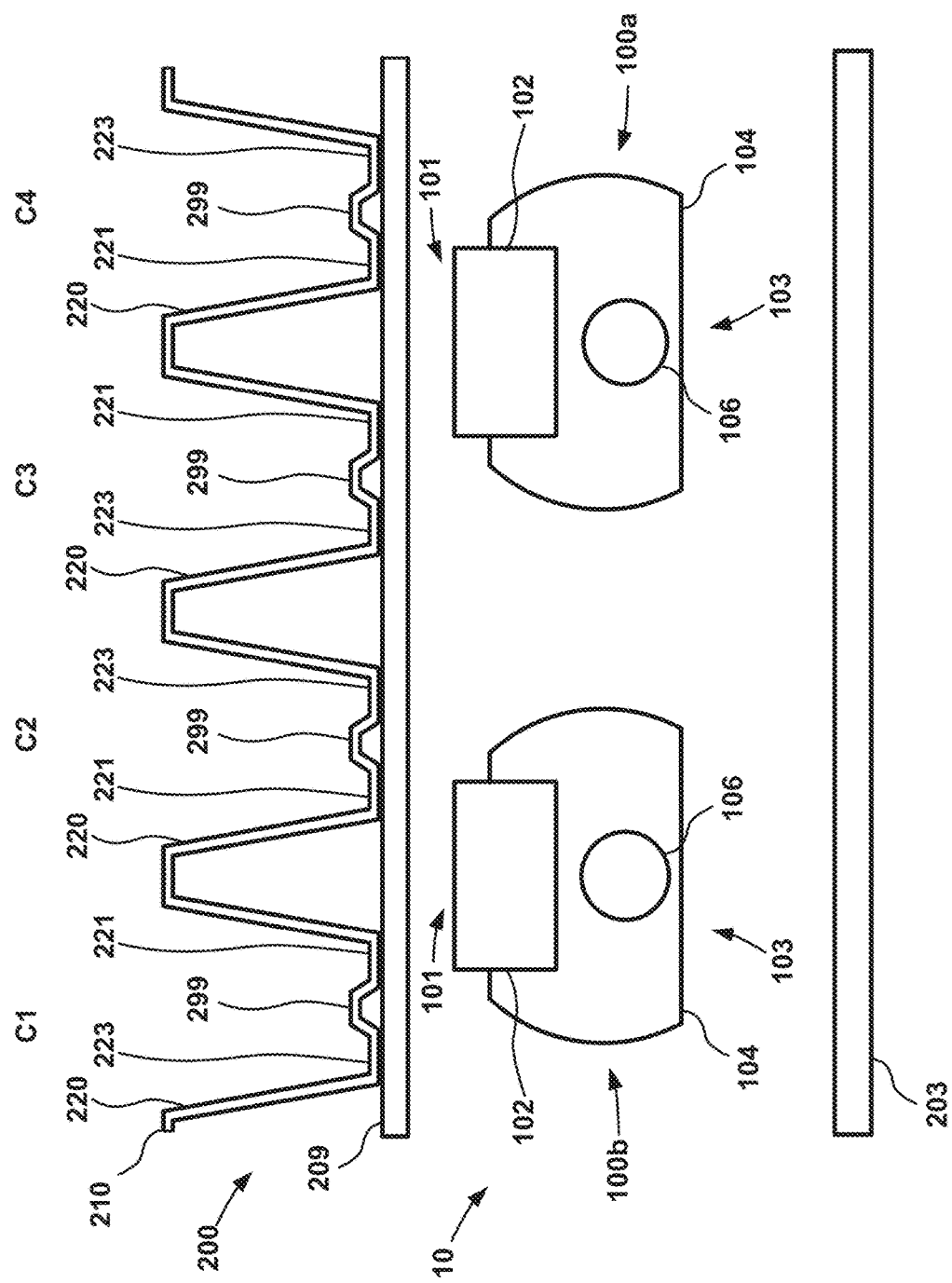
Figure 10:
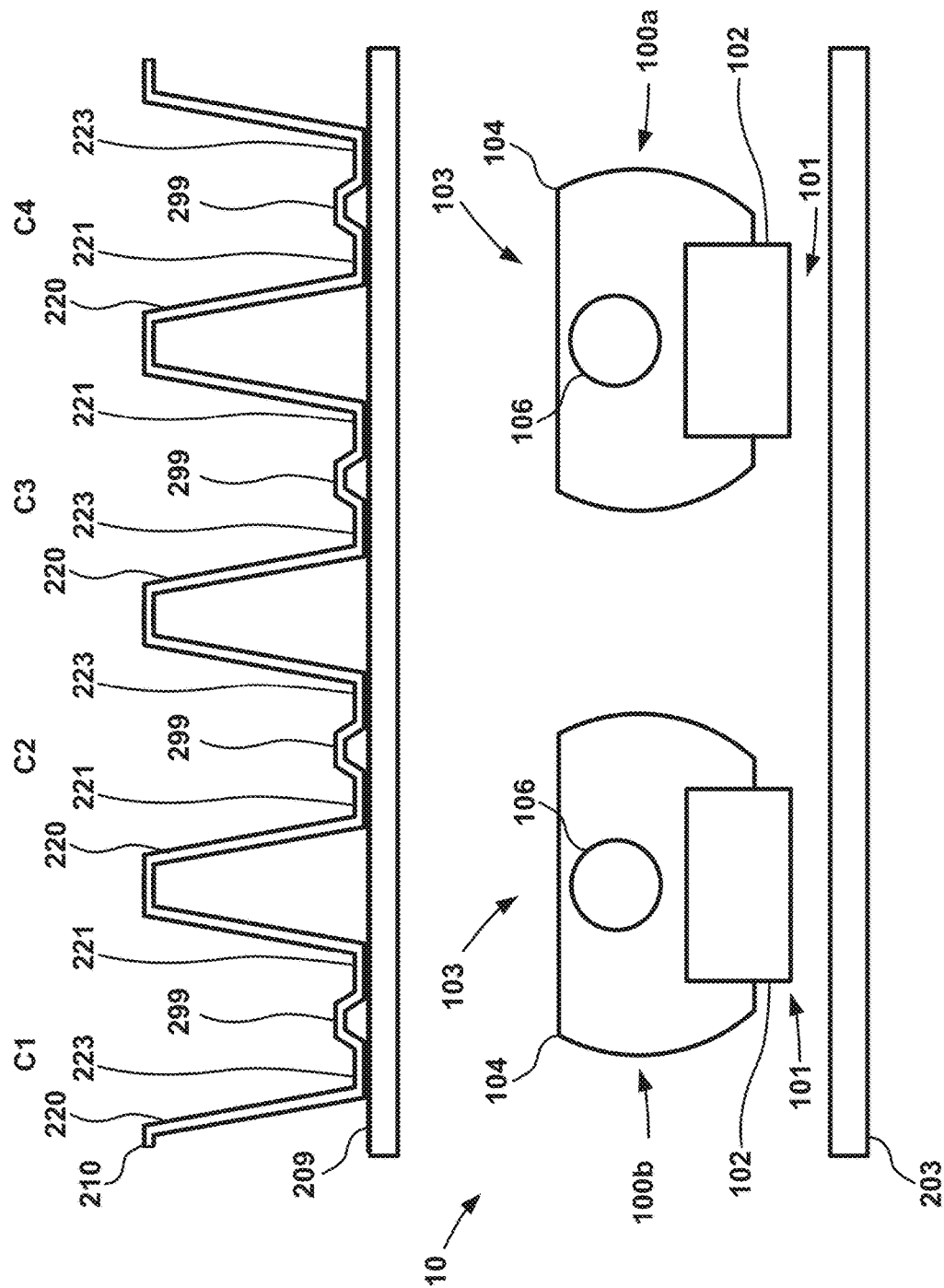
FIG. 10 is an end view of a portion of the embodiment of FIG. 5A and a well plate showing shielded magnets in a second position.

FIGS. 9 and 10 are schematic illustrations of magnetic actuator 10, which is configured for use in an assay preparation module 200, shown in end view. Support and gear elements are not shown for clarity, and these embodiments depict only two shielded magnets 100a and 100b. In other embodiments, however, only one magnet may be used or there may be three, four, five, six, seven, eight, nine, ten, eleven, twelve or more shielded magnets.

Magnetic actuator 10 is depicted within assay preparation module 200. A partial well plate 210 is shown supported by well plate platform 209.

Well plate 210 comprises a plurality of reaction wells 220. Well plate 210 may comprise forty-eight wells 220 (eight columns C1-C8 by six rows R1-R6) as shown in FIG. 11. Other embodiments of the well plates that may be used with the present systems may comprise ninety-six, one hundred ninety-two, or some other number of wells 220.

In certain exemplary embodiments, each well 220 of well plate 210 comprises a proximal trench 221 (the trench closest to a magnet array 100) and a distal trench 223 (the trench furthest from a magnet array 100) separated by a ridge 299. In other embodiments, wells 220 may have a flat bottom, a U-shaped bottom, a V-shaped bottom, a rounded bottom, or any other suitable profile.

In the illustrated embodiment, well plate 210 is configured to be placed above magnetic actuator 10 on well plate platform 209 in assay preparation module 200 such that each shielded magnet (e.g., 100a, 100b) is adjacent and substantially parallel to two columns of wells 220. For example, second shielded magnet 100b may be adjacent and substantially parallel to columns C1 and C2, first shielded magnet 100a may be adjacent and substantially parallel to columns C3 and C4, third shielded magnet 100c may be adjacent and substantially parallel to columns C5 and C6, and fourth shielded magnet 100d may be adjacent and substantially parallel to columns C7 and C8. In this configuration, a pellet of magnetic particles (not shown) may be formed substantially in each proximal trench nearest the corresponding magnet array, while the fluid may be aspirated from each distal trench furthest from the corresponding magnet array.

In other embodiments, shielded magnets may be adjacent and substantially parallel to two rows of wells 220 (rather than two columns of wells as described above). In still other embodiments, a shielded magnet may correspond to each row R or column C of wells 220. In still other embodiments, a shielded magnet may correspond to each individual well 220.

In FIG. 9, magnetic actuator 10 is shown in a first position (e.g. the "max state") adjacent to a portion of well plate 210. Second shielded magnet 100b is shown adjacent and substantially parallel to columns C1 and C2, while first shielded magnet 100a is shown adjacent and substantially parallel to columns C3 and C4. In the first position, the shielded magnets are positioned (e.g., have been rotated about an axis) such that top side 101 is closer to wells 220 in a given pair of columns than bottom side 103 is. While in the first position, each permanent magnet 102 applies a magnetic field to wells 220.

In FIG. 10, magnetic actuator 10 is in a second position (e.g. the "min state") adjacent to a portion of well plate 210. Second shielded magnet 100b is shown adjacent and substantially parallel to columns C1 and C2, while first shielded magnet 100a is shown adjacent and substantially parallel to columns C3 and C4. In the second position, the shielded magnets are positioned (e.g., have been rotated about an axis) such that bottom side 103 is closer to wells 220 than top side 101 is, and that shield 104 is between permanent magnet 102 and wells 220.

While in the second position, each permanent magnet 102 applies a smaller magnetic field to wells 220 than when in the first position, both because shield 104 reduces the magnetic field and because permanent magnet 102 is further away from wells 220 than when in the first position. In certain embodiments, the magnetic field from some or all of permanent magnets 102 that is applied to wells 220 in the min state may be zero or so small as to exert no detectable effect on the contents of wells 220.

In certain embodiments of the present actuators, the motors are configured to rotate the shielded magnets such that each shielded magnet is either in the first position (which may be considered the "on" position) or the second position (which may be considered the "off" position). Such embodiments may be referred to as having a "binary" configuration. In other embodiments of the present actuators, the motors are configured to rotate the shielded magnets such that each shielded magnet can be positioned anywhere between and including the first and second positions. Such embodiments may be referred to as having an analog configuration.

Referring back to actuator 10, the embodiment of the present actuators shown in FIGS. 1 and 5A, rotation motor 30a is configured to rotate first gear 41a clockwise, which rotates second gear 42a and first shielded magnet 100a counterclockwise. ("Clockwise" and "counterclockwise" are relative terms; here, the viewer is presumed to be looking at magnetic actuator 10 from an end such that a given gearset is between the viewer and the shielded magnet). Second gear 42a rotates third gear 43a clockwise, which rotates fourth gear 44a and second shielded magnet 100b counterclockwise. In this manner, the shielded magnets are configured to rotate counterclockwise away from the rotation motors to minimize magnetic interference. In other embodiments, the system may be configured such that the shielded magnets may be configured to rotate independently from one another. In still other embodiments, three, four, five, six, seven, eight, nine, ten, eleven, twelve, or more shielded magnets may be coupled to the same gearset such that all the shielded magnets coupled to a gearset can be rotated together.

In the illustrated embodiment, the shielded magnet of actuator 10 furthest from the rotation motor to which it is coupled is coupled to a position indicator. Thus, in the embodiment shown, second shielded magnet 100b is coupled to first position indicator 22a and fourth shielded magnet 100d is coupled to second position indicator 22b. The position indicator rotates with the shielded magnet to which it is coupled and is located adjacent to two sensors—left sensor 21b and right sensor 23b; though not shown, comparable left and right sensors may be positioned in the same respective locations with respect to first position indicator 22a. Left sensor 21b and right sensor 23b are coupled to a processor and are configured to send a signal to the processor when the sensor is tripped. In various embodiments, one sensor may be used, or three or more sensors may be used. In various embodiments, a photointerrupter, a fiber optic sensor, a reflective optical sensor, an encoder, a mechanical switch, a Hall effect sensor, a magnetic field sensor, or other suitable binary position sensors known to those of ordinary skill in the art may be used for each sensor.

In the illustrated embodiment, sensors 21b and 23b are photointerruptor-type sensors. Each sensor is configured to emit a beam of light from an emitter and is configured to receive the beam with a receiver. In the embodiment shown, a sensor is "occluded" when the beam is not allowed to pass from the emitter to the receiver, e.g., is blocked with a position indicator. A sensor is "not occluded" when the beam is allowed to pass from the emitter to the receiver.

Thus, together with the sensors, the position indicators may be used to indicate the position or state of each of a given shielded magnet or a given pair of shielded magnets. In the illustrated embodiment, each shielded magnet has one of three possible positions or states: a first position (e.g. a max state), a second position (e.g. a min state), and an intermediate state between the first and second positions. The two sensors associated with each position indicator each have two possible states (occluded and not occluded), thus allowing four possible state combinations. In the configuration shown, the state in which both sensors are not occluded is not possible since the magnets are configured to rotate only about 180 degrees. Therefore, the three possible sensor states are able to uniquely identify the three possible magnet states of min, max, and intermediate.

For example, in the illustrated embodiment, when left sensor 21b is not occluded and sensor 23b is occluded, shielded magnets 100c and 100d are in the max state. When right sensor 23b is not occluded, and left sensor 21b is occluded, shielded magnets 100c and 100d are in the min state. When both left sensor 21b and right sensor 23b are occluded, shielded magnets 100c and 100d are moving between the max and min states and are in the intermediate state. In FIG. 1, third shielded magnet 100c and fourth shielded magnet 100d are shown in the min state. Accordingly, second position indicator 22b is shown with right sensor 23b not occluded and left sensor 21b occluded.

In other embodiments, the position indicators may not be necessary and only one sensor (rather than the two sensors shown) may correspond to each synchronously rotating set of shielded magnets. In such embodiments, the sensor may be a variable position sensor configured to indicate the position of each set of shielded magnets. The position of each set of shielded magnets corresponds to the strength of the magnetic field those magnets exert on wells 220. Accordingly, in such embodiments, each sensor may be tuned to an intermediate position between the max state and the min state. In various embodiments, sensors may include rheostats, encoders, Hall effect sensors, potentiometers, or other suitable variable position sensors known to those of ordinary skill in the art.

In the embodiments of the present shielded magnets shown in FIGS. 1-10, the poles of adjacent permanent magnets 102 alternate (e.g., poles alternate N-S-N-S in the max state, etc.). In simulations of the embodiment illustrated in FIGS. 1, 5, and 6, this configuration produces a higher max strength than a configuration where all poles are aligned alike, but also produces a higher min strength. Furthermore, in simulations of this embodiment, the magnets are in stable equilibrium in both the max and min state.

In other configurations, the poles of all permanent magnets 102 may be aligned alike (e.g., all N poles are up in the max state). In simulations of the embodiment illustrated in FIG. 1, this configuration produces the lowest min strength (the strength of the magnetic field exerted on wells 220 when shielded magnets 100 are in the min state), though the max strength (the strength of the magnetic field exerted on wells 220 when shielded magnets 100 are in the max state) is less than the theoretical maximum. According to simulations of the illustrated embodiment, this configuration produces the greatest differential between max strength and min strength.

Methods for Collecting a Sample of Magnetic Particles

FIG. 12 illustrates steps of an embodiment of a method 1000 for collecting a sample of magnetic particles from a liquid. Step 1002 comprises obtaining a system comprising a chassis; a magnetic actuator coupled to the chassis; a tub coupled to the chassis; an agitator motor coupled to the chassis and configured to agitate the tub; and a well plate coupled to the tub and comprising a plurality of wells arranged in columns and rows; where the tub is configured to support the well plate such that each shielded magnet is adjacent to at least one column of wells. Step 1004 comprises obtaining a first suspension comprising a plurality of magnetic particles suspended in a first liquid. Step 1006 comprises introducing a volume of the first suspension into at least one well. Step 1008 comprises rotating the shielded magnets to a max state such that each permanent magnet exerts a magnetic force on at least one column of wells. Step 1010 comprises forming a pellet of magnetic particles in at least one well. Step 1012 comprises aspirating a portion of the first liquid from at least one well. Step 1014 comprises rotating the shielded magnets to a min state such that substantially no magnetic force is exerted on any column of wells. Step 1016 comprises obtaining a second liquid. Step 1018 comprises introducing the second liquid into at least one well comprising magnetic particles. Step 1020 comprises agitating the magnetic particles in at least one well to form a second suspension comprising the magnetic particles suspended in the second liquid. These steps may be performed in the order listed but need not be.

It should be understood that the present devices and methods are not intended to be limited to the particular forms disclosed. Rather, they are to cover all modifications, equivalents, and alternatives falling within the scope of the claims. For example, certain embodiments of the present magnetic actuators, such as actuator 10, discussed above are shown configured for use with a well plate in an assay preparation module. However, magnetic actuator 10 is suitable for use in any small space where a controllable magnetic field may be required.

The above specification and examples provide a complete description of the structure and use of exemplary embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the present devices are not intended to be limited to the particular forms disclosed. Rather, they include all modifications and alternatives falling within the scope of the claims, and embodiments other than the one shown may include some or all of the features of the depicted embodiment. For example, components may be combined as a unitary structure and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not to be interpreted as including means-plus- or step-plus-function limitations, unless such a limitation is explicitly recited in a given claim using the phrase(s) "means for" or "step for," respectively.

We claim:

1. A system configured to isolate particles in a fluid assay comprising:
   a chassis;
   a magnetic actuator coupled to the chassis, the magnetic actuator having rotatable shielded magnets, wherein each of the rotatable shielded magnets comprises:
   a top surface;
   a bottom surface; and a shield, wherein the shield covers the bottom surface and is directly coupled to the rotatable shielded magnet;

a tub coupled to the chassis; and a well plate coupled to the tub and comprising a plurality of wells arranged in columns and rows;

where the tub is configured to support the well plate such that each shielded magnet is adjacent to at least one column of wells.

2. The system of claim 1 where:

a rotatable shielded magnet is configured to rotate from a first position to a second position;

the rotatable shielded magnet exerts a first magnetic field on the well plate in the first position;

the rotatable shielded magnet exerts a second magnetic field on the well plate in the second position; and the first magnetic field is greater than the second magnetic field.

3. The system of claim 2 where:

at least one well comprises a plurality of magnetic microspheres;

the first magnetic field is sufficient to move the plurality of magnetic microspheres; and the second magnetic field is not sufficient to move the plurality of magnetic microspheres.

4. The system of claim 1, where each rotatable shielded magnet is adjacent to two columns of wells.

5. The system of claim 1, where:

each rotatable shielded magnet comprises a permanent magnet;

the shield is coupled to and covers a portion of the permanent magnet; and each rotatable shielded magnet has a thickness, a length, and an axis of rotation.

6. The system of claim 5 where the axis of rotation is an eccentric axis of rotation.

7. The system of claim 5, where the shield comprises a magnetic permeable material, the permanent magnet comprises a rare earth material, and the permanent magnet is magnetized through its thickness.

8. The system of claim 1, further comprising an agitator motor and a link coupled to the tub, where the agitator motor and the link are configured to agitate the tub and the well plate during operation.

* * * * *